United States Patent [19]

Spicer et al.

[11] 3,953,606

[45] Apr. 27, 1976

[54] COMPOSITIONS AND METHOD OF USING UREIDOTETRALIN COMPOUNDS OR DERIVATIVES THEREOF

[75] Inventors: Larry Dean Spicer, Princeton; Joseph Michael Pensack, Trenton; Robert Daniel Wilbur, Titusville, all of N.J.; Gary Michael Demkovich, deceased, late of Cranbury, N.J., by Ruth Ellen Demkovich, administratrix

[73] Assignee: American Cyanamid Company, Stamford, Conn.

[22] Filed: Feb. 7, 1974

[21] Appl. No.: 440,626

[52] U.S. Cl. .............................................. 424/322
[51] Int. Cl.² ........................................... A61K 31/17
[58] Field of Search .................................. 424/322

[56] References Cited

UNITED STATES PATENTS

| | | | |
|---|---|---|---|
| 2,870,159 | 1/1959 | Bloom | 260/307 |
| 2,889,351 | 6/1959 | Bloom | 260/456 |
| 2,956,072 | 10/1960 | Bloom | 260/456 |

OTHER PUBLICATIONS

*Journal of the Chemical Society Abstracts,* 114, 418 (1918).

*Primary Examiner*—Frederick E. Waddell
*Attorney, Agent, or Firm*—Edward A. Conroy, Jr.

[57] ABSTRACT

This invention relates to a method for enhancing the growth rate of animals, particularly farm animals such as livestock, by administering to said animals compositions containing a growth-enhancing amount of a ureidotetralin compound or derivative thereof.

14 Claims, No Drawings

COMPOSITIONS AND METHOD OF USING UREIDOTETRALIN COMPOUNDS OR DERIVATIVES THEREOF

SUMMARY OF THE INVENTION

This invention relates to a novel method for enhancing the growth rate of animals and improving feed efficiency therefor. More particularly, this invention relates to a method for enhancing the growth rate and improving the feed efficiency of animals by administering to said animals a growth promoting amount of a compound having the formula:

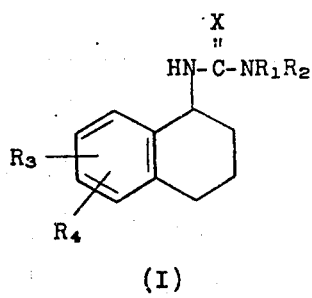

(I)

wherein X is sulfur or oxygen; $R_1$ is hydrogen or alkyl $C_1$-$C_4$; $R_2$ is hydrogen, alkyl $C_1$-$C_4$, alkoxy $C_1$-$C_4$, benzyl or benzyloxy; $R_3$ is hydrogen, alkyl $C_1$-$C_4$ or alkoxy $C_1$-$C_4$; and $R_4$ is hydrogen or alkyl $C_1$-$C_4$. In practice, we have found that the active compound may be used in its racemic form or it may be administered as the optically active (S) isomer of I.

The two optically active forms designated as the (R) and the (S) isomer are illustrated below.

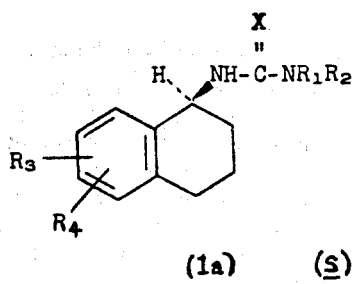

(Ia)  (S)

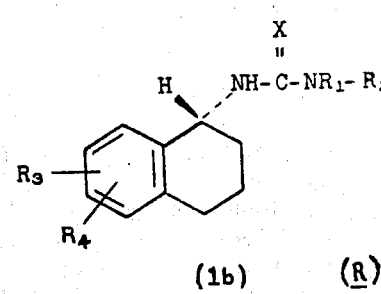

(Ib)  (R)

wherein X, $R_1$, $R_2$, $R_3$ and $R_4$ are as described above.

The (S) urea derivatives have the useful biological activity while the (R) ureas have little or no growth-promoting activity but contribute some toxicity to the racemic form.

The preferred compounds are the ureas derived from the unsubstituted 1,2,3,4-tetrahydro-1-naphthylamine, and particularly the (S) optically active isomers thereof. The (S) isomers are the preferred form of the active component since they have the best growth promoting potential. They also have the important advantage that it requires only onehalf as much (S) isomer as it does of the racemic mixture for a given response.

Except for the resolution of the intermediate, 1,2,3,4-tetrahydro-1-naphthylamine, into its optically active isomers, the compounds are generally prepared from common and readily available starting materials and are made by chemical reactions that are well known to those skilled in the art. For example, G. Schroeter and K. Thomas, *Journal of the Chemical Society Abstracts* 114: 418 (1918), have prepared the urea from 1,2,3,4-tetrahydro-1-naphthylamine with potassium cyanate. Useful preparative methods are illustrated by the following equations:

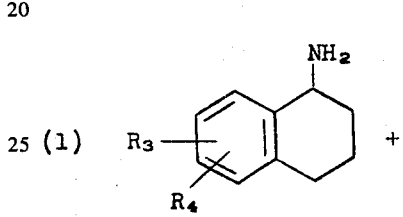

(1) 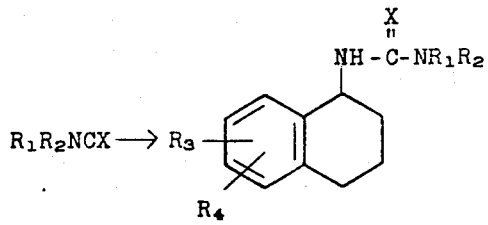

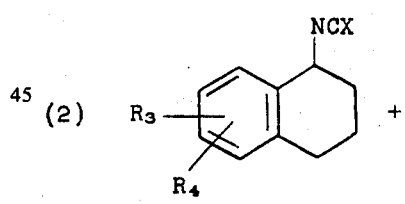

(2) 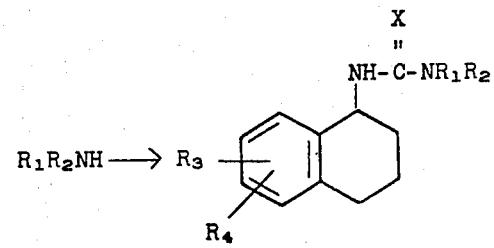

wherein X, $R_1$, $R_2$, $R_3$ and $R_4$ are as defined above.

The urea obtained has the same absolute configuration at the 1- position of the 1,2,3,4-tetrahydronaphthylene as the 1,2,3,4-tetrahydro-1-naphthylamine used as starting material. In order to obtain the desired (S) isomer of the urea, it is necessary to start with the (S) isomer of the 1-amino-1,2,3,4-tetrahydronaphthalene, which can be reacted with RNCO to form the (S) urea directly or with phosgene to yield the (S) isomer of the isocyanate, which is then reacted with $R_1R_2NH$ to yield an identical product.

Resolved 1,2,3,4-tetrahydro-1-naphthylamines have been reported in the published literature [R. Weidmann and J. -P. Guetté, *Comptes Rendus des Séances de l'Académie des Sciences* 268: 2225 (1969)] as resulting from the Curtius reaction with the optically active 1,2,3,4-tetrahydronaphthalene carboxylic acid azides. This work establishes the absolute configuration of the (R) and (S) isomers, but does not provide a practical preparative method for preparing the isomers in a high state of purity. We have found that 1,2,3,4-tetrahydro-1-naphthylamine can be separated into its optical isomers through the appropriate N-benzoyl glutamic acid salt. The (S) -(+)- 1,2,3,4-tetrahydro-1-naphthylamine forms a water-insoluble salt with (+)N-benzoyl-(R)-glutamic acid which can be crystallized out in high yield while the (R) amine salt stays in solution. It is not necessary to employ more than about 1 mole of the resolving acid for each 2 moles of racemic amine, as a cheaper acid, preferably acetic, can be substituted for the balance of the required acid. In this way it is possible to obtain a high yield of the desired (S)-(+) amine based on the resolving acid. The resolved salt, (S)-1,2,3,4-tetrahydro-1-naphthylamine N-benzoyl-(R)-glutamic acid salt is treated with alkali which liberates the (S)-(+) amine which separates as an insoluble phase. It can be mechanically separated from the aqueous layer or extracted with a suitable solvent.

The compounds of this invention are useful for enhancing the growth rate and feed efficiency in a wide variety of animals including ruminant livestock, poultry and fur-bearing animals. The active compounds can be administered to said animals incorporated in their diet, implanted in the form of one or several pellets under the skin of the animal, or injected subcutaneously or intramuscularly in the form of a paste, solution or suspension.

When administered with the animal diet, generally about 25 ppm to 800 ppm, and preferably 50 ppm to 200 ppm, of the drug is effective for increasing weight gains of the treated animals. It is, of course, obvious that the growth promoter may be formulated as a premix, supplement or concentrate, with other edible carriers such as ground corn, soybean meal, fish meal, and the like, and then mixed with or added to the animal feed at the feeding site. In such concentrate formulations, the growth promoter may amount to from about 1% to 30% by weight of the formulation. The active component may also be prepared as a pellet for implantation under the animal's skin. Usually, about a 1:1 or higher ratio of the growth promoter and a pharmaceutically acceptable carrier such as castor wax are blended. The blended maerial is then pressed into the form of a pellet, which is introduced singly or in multiple doses with a pellet injector under the animal's skin. The pellet generally contains about 5 mg to 100 mg, and preferably 10 mg to 30 mg, of the ureidotetralin, which is slowly released into the animal's system following implantation.

With this method of application, the growth promoter can be administered at periodic intervals throughout the feeding period of the animals. Formulations and intervals between implantations can be varied to provide a daily ureidotetralin release of generally about 0.001 mg to 0.2 mg per kg of body weight, and preferably 0.01 mg to 0.10 mg per kg of body weight.

DETAILED DESCRIPTION

The present invention is further illustrated by the preparation of representative examples set forth below, as well as testing data on typical compounds of the invention.

EXAMPLE 1

Preparation of
1-Ethyl-3-(1,2,3,4-tetrahydro-1-naphthyl)urea

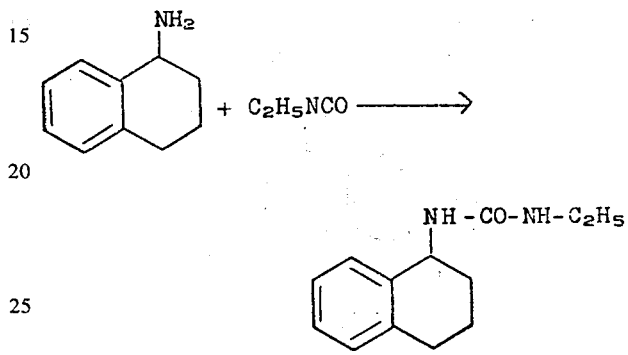

A sample of 1,2,3,4-tetrahydro-1-naphthylamine (7.4 grams, 0.05 mole) is dissolved in 140 ml of ether and treated with a solution of ethyl isocyanate (3.6 grams, 0.05 mole) in 10 ml of ether. The reaction mixture is stirred at reflux for 3 hours, and then overnight at room temperature. The crude product is collected by filtration and recrystallized from a hot mixture of methanol and water. The yield is 7.8 grams (71.6%), melting point 178°C. to 179°C.

EXAMPLE 2

Preparation of
1-Ethyl-3-(1,2,3,4-tetrahydro-1-naphthyl)- thiourea

To a stirred solution of 8.84 grams (0.060 mole) of 1,2,3,4-tetrahydro-1-naphthylamine in 100 ml of acetone, under a blanket of nitrogen, is added a solution of 6.27 grams (0.072 mole) of ethyl isothiocyanate in 50 ml of acetone. The reaction mixture is stirred overnight, and the solvent then evaporated at reduced pressure. Toluene is added to the residue, and the mixture is then evaporated at reduced pressure. The residue is crystallized from nitromethane to give 7.08 grams of the product, melting point 120°C. to 122°C.

EXAMPLE 3

Preparation of 1,2,3,4-Tetrahydro-1-naphthyl Isocyanate

To a stirred solution of 242.4 grams (2.46 moles) of phosgene in 200 ml of toluene and 600 ml of benzene is slowly added a solution of 119.9 grams (0.814 mole) of 1,2,3,4-tetrahydro-1-naphthylamine, while maintaining the reaction temperature at 10°C. to 15°C. The mixture is stirred overnight at room temperature and then heated to reflux under a nitrogen atmosphere. After 4 hours reflux, most of the solvent is distilled from the reaction at atmospheric pressure. The residual solvent is evaporated at reduced pressure. The crude product is distilled to give 121.4 grams of product with boiling point 90°C. to 96°C. (0.3 mm).

EXAMPLE 4

Preparation of
1-Methoxy-3-(1,2,3,4-tetrahydro-1-naphthyl)urea

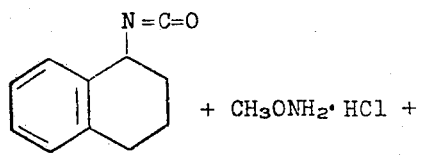

+ CH₃ONH₂·HCl +

N(C₂H₅)₃ →

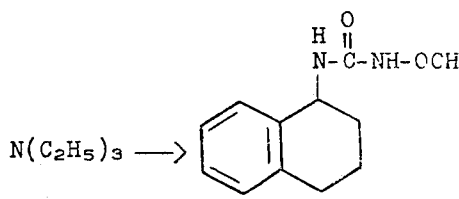

To an ice-cold, stirred mixture of 6.7 grams (0.080 mole) of methoxyamine hydrochloride in 80 ml of methylene chloride is added a solution of 8.1 grams (0.080 mole) of triethylamine in 20 ml of methylene chloride. The mixture is stirred at 15°C. for 15 minutes, and is then allowed to warm to 15°C. to 25°C. while a solution of 6.94 grams (0.04 mole) of 1,2,3,4-tetrahydro-1-naphthyl isocyanate in 25 ml of methylene chloride is added dropwise. The mixture is stirred for 30 minutes at room temperature and then filtered. The filtrate is washed with water, dried (sodium sulfate), and the solvent evaporated at reduced pressure to give a solid. Recrystallization of the solid from acetone/hexane gives 6.75 grams of the product, melting point 122°C. to 125°C. Recrystallization of the product from acetone/hexane gives the analytical sample, melting point 123.5°C. to 125°C.

EXAMPLE 5

Preparation of
1,1-Dimethyl-3-(1,2,3,4-tetrahydro-1-naphthyl urea

To a stirred mixture of 7.1 grams (0.05 mole) of 1,2,3,4-tetrahydro-1-naphthylamine, 7 ml (0.05 mole) of triethylamine and 100 ml of benzene is added, dropwise, 5.5 grams (0.05 mole) and dimethylcarbamyl chloride. The mixture is stirred for one day at ambient temperature and then filtered to remove triethylamine hydrochloride. The filter cake is washed with benzene. Evaporation of the filtrate at reduced pressure gives a white solid. The solid is recrystallized from toluene to give the product, melting point 139°C. to 140°C.

EXAMPLE 6

Preparation of
(S)-1,2,3,4-Tetrahydro-1-naphthylamine
N-Benzoyl-(R)-glutamic Acid Salt

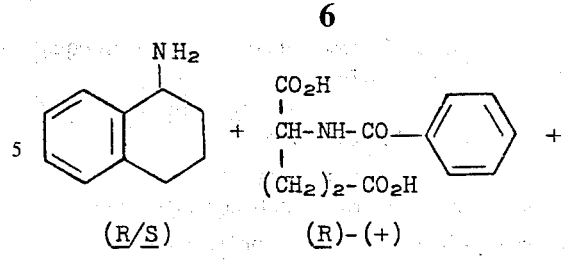

CH₃CO₂H ——→

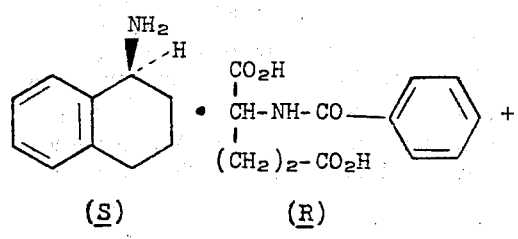

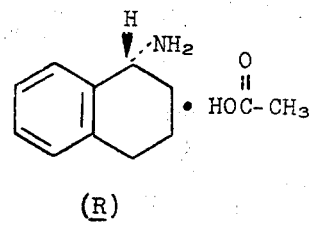

A stirred mixture of 284 grams (1.13 moles) of (R)-(+)-N-benzoylglutamic acid, 136 grams (2.26 moles) of acetic acid, and 2 liters of water is heated to 55°C. to give a solution. To this stirred solution is added 333 grams (2.26 moles) of racemic 1,2,3,4-tetrahydro-1-naphthylamine.

After an initial mild rise in reaction temperature, the crystalline salt precipitates. The mixture is stirred and allowed to cool over a period of about 1 hour. The mixture is cooled to 25°C., filtered, washed with cold ethanol and dried to give 396.3 grams of the (S)-1,2,3,4-tetrahydro1-naphthylamine N-benzoyl-(R)-glutamic acid salt, melting point 204°C. to 210°C. The following rotations are obtained on the product: $[\alpha]_D^{28}$ −10.0° (c 3, HOAc); $[\alpha]_{436}^{28}$ −30.1°(c 3, HOAc); $[\alpha]_{365}^{28}$ −58.4° (c 3, HOAc).

EXAMPLE 7

Preparation of
(R)-1,2,3,4-Tetrahydro-1-naphthylamine
N-Benzoyl-(S)-glutamic Acid Salt Following the procedure of Example 6, but substituting N-benzoyl-(S)-glutamic acid for N-benzoyl-(R)-glutamic acid, yields the (R)-1,2,3,4-tetrahydro-1-naphthylamine N-benzoyl-(S)-glutamic acid salt. The melting point and yield of this product are the same as obtained in Example 6; however, the salt has an equal but opposite optical rotation.

EXAMPLE 8
Preparation of (S)-(+)-1,2,3,4,-Tetrahydro-1-naphthylamine

A slurry of 130.3 grams (0.36 mole) of (S)-1,2,3,4-tetrahydro-1-naphthylamine N-benzoyl-(R)-glutamic acid salt in ice and water is made basic by the addition of a cold solution of 34.0 grams (0.847 mole) of sodium hydroxide in water. The liberated amine is extracted with ether. The ether solution is dried over a mixture of magnesium sulfate and sodium hydroxide pellets. The ether is evaporated, and the amine distilled to give the product boiling point 72°C. to 77°C. at 0.6 mm, $[\alpha]_D^{25} + 54.9°$ (c 5.2, benzene).

EXAMPLE 9
Preparation of (R)-(−)-1,2,3,4-Tetrahydro-1-naphthylamine

The (R) amine is made in the same way as described in Example 8, but from the salt from N-benzoyl-(S)-glutamic acid. It has $[\alpha]_D^{25}$ -54.0° (c 5.1, benzene).

EXAMPLE 10
Preparation of (S)-(−)-1-Methyl-3-(1,2,3,4-tetrahydro-1-naphthyl)urea

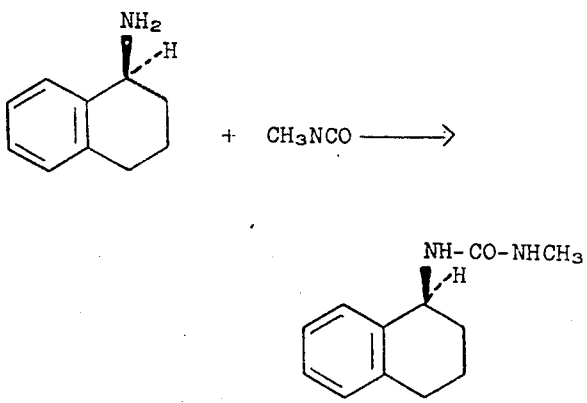

To a stirred solution of 17.7 grams (0.12 mole) of (S)-(+)-1,2,3,4-tetrahydro-1-naphthylamine in 500 ml ether, maintained under a nitrogen atmosphere, is added a solution of 8.0 ml (0.135 mole) of methyl isocyanate in 250 ml of ether over a 20-minute period. An additional 200 ml of ether is added, and the mixture is stirred for 30 minutes. The mixture is filtered, and the filter washed with ether and then dried to give 23.3 grams of product, melting point 193°C. to 195°C. The following rotations are obtained on the product: $[\alpha]_D^{25}$ −30.0° (c 5, HOAc); $[\alpha]_{436}^{25}$ −73.0° (c 5, HOAc) $[\alpha]_{365}^{25}$ −136° (c 5, HOAc).

EXAMPLE 11
Preparation of (S)-(−)-1,2,3,4-Tetrahydro-1-naphthylurea

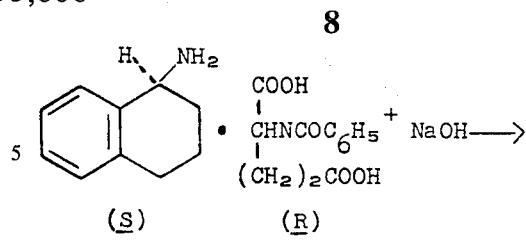

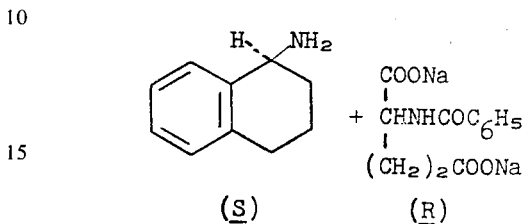

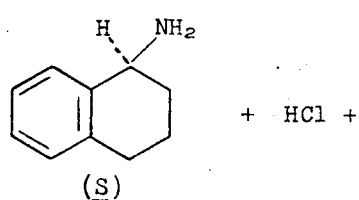

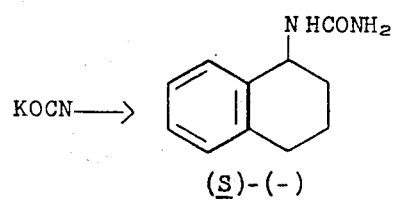

(S)-Amine-(R)-acid salt (1149 grams, 2.88 moles) is placed in a 12-liter separation tunnel. Ice (300 grams) is added, followed by 346 grams (8.65 moles, 3 equivalents) of NaOH in 870 ml of water. The mixture is shaken, and the liberated amine extracted with 4 liters of ether. The aqueous phase is extracted with an additional 2 liters of ether. The combined ether extracts are washed with saturated sodium chloride solution. The ether solution is then cooled with ice, and the amine extracted with 288 ml HCl in 2 liters of water (3.46 moles of HCl, 20% excess). The ether layer is washed with 800 ml of water. The combined aqueous phases containing the amine hydrochloride are placed in a 1-liter reaction flask. The reaction mixture is cooled to 5°C., and a solution of 280 grams (3.46 moles, 20% excess) of potassium cyanate in 1.5 liters of water is added through a dropping tunnel. The cooling bath is removed, and the reaction mixture warmed to 70°C. to 80°C. The reaction mixture is then left standing overnight at room temperature. The urea is recovered by filtration, washed with water, and then with cold isopropanol. The yield is 457 grams (2.40 moles, 83%), melting point 197°C. to 204°C., $[\alpha]_D^{25}$ −35.2° (c 5, HOAC); $[\alpha]_{436}^{25}$ −85.4° (c 5, HOAc).

EXAMPLES 12–24

Following the procedure of Example 1 or 2 above, but substituting the appropriate naphthylamine for 1,2,3,4-tetrahydro-1-naphthylamine and the appropriate isocyanate or isothiocyanate for ethyl isocyanate or ethyl isothiocyanate, yields the following compounds having the structure:

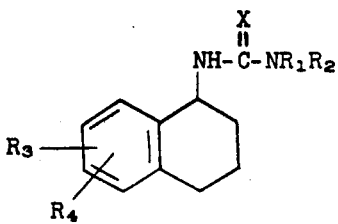

| X | $R_1$ | $R_2$ | $R_3$ | $R_4$ | Melting Point °C |
|---|---|---|---|---|---|
| O | $CH_3$ | H | H | H | 173–175 |
| O | H | H | H | H | 212–214 |
| O | H | $-C_3H_7-n$ | H | H | 141–143 |
| O | H | $CH_3-CH-C_2H_5$ | H | H | 171–172 |
| O | $C_2H_5$ | H | 6-$OCH_3$ | H | 165–170 |
| O | $C_2H_5$ | $C_2H_5$ | H | H | 86–87 |
| O | H | H | 5-$OCH_3$ | H | 225–226 |
| O | $C_2H_5$ | H | 5-$OCH_3$ | H | 190–191 |
| O | H | $-CH_2C_6H_5$ | H | H | 179–182 |
| O | H | $CH_3$ | 6-$CH_3$ | 7-$CH_3$ | 215–216 |
| O | H | $C_2H_5$ | 6-$CH_3$ | 7-$CH_3$ | 204–205.5 |
| O | H | H | 5-$CH_3$ | 7-$CH_3$ | 231–232 |
| O | H | $CH_3$ | 5-$CH_3$ | 7-$CH_3$ | 196–198 |

EXAMPLE 25

Mouse Growth Regulant Tests

CFI female mice from Carworth Farm are received when they are six weeks old. They are housed ten to a cage in air-conditioned rooms (72°F. to 76°F.) with automatically controlled lights, 14 hours on and 10 hours off. The basal diet used in these studies is Purina Laboratory Chow (see description below), which is supplied ad libitum. Water is also allowed ad libitum.

Thirteen days after arrival, the mice are weighed in groups of ten and assigned at random to the different treatments. The concentration of the different compounds in the diet is indicated in the enclosed Tables. Twelve days later the mice are weighed again and the experiment terminated. At least three cages (30 mice) of untreated controls are included in each test. Test data for representative compounds are summarized in the Table below.

Diet
GUARANTEED ANALYSIS

| | |
|---|---|
| Crude protein no less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE I

Mouse Growth Regulant Test with Compounds Having the Structure:

| X | $R_1$ | $R_2$ | $R_3$ | $R_4$ | Dietary Level ppm | % Weight Gain Over Controls |
|---|---|---|---|---|---|---|
| O | H | $C_2H_5$ | H | H | 100 | 21.4 |
|   |   |   |   |   | 200 | 43.0 |
|   |   |   |   |   | 400 | 64.6 |
| O | $CH_3$ | H | H | H | 50 | 20.2 |
|   |   |   |   |   | 100 | 87.1 |
|   |   |   |   |   | 200 | 66.8 |
|   |   |   |   |   | 400 | 87.1 |
| O | H | H | H | H | 50 | 30.0 |
|   |   |   |   |   | 100 | 50.9 |
|   |   |   |   |   | 200 | 67.5 |
|   |   |   |   |   | 400 | 20.0 |
|   |   |   |   |   | 800 | 114.7 |
| O | H | $-C_3H_7-n$ | H | H | 100 | 65.3 |
|   |   |   |   |   | 200 | 49.5 |
|   |   |   |   |   | 400 | 80.4 |
| S | $C_2H_5$ | H | H | H | 100 | 45.0 |
|   |   |   |   |   | 200 | 30.0 |
|   |   |   |   |   | 400 | 84.9 |
| O | $CH_3$ | $CH_3$ | H | H | 100 | 16.4 |
|   |   |   |   |   | 200 | 21.4 |
|   |   |   |   |   | 400 | 9.2 |

TABLE I-continued

Mouse Growth Regulant Test
with Compounds Having the Structure:

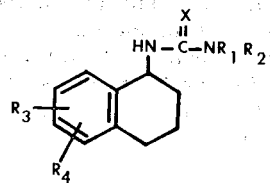

| X | $R_1$ | $R_2$ | $R_3$ | $R_4$ | Dietary Level ppm | % Weight Gain Over Controls |
|---|---|---|---|---|---|---|
| O | H | $-\underset{\underset{CH_3}{\mid}}{CH}-C_2H_5$ | H | H | 100 | 37.5 |
|   |   |   |   |   | 200 | 46.0 |
|   |   |   |   |   | 400 | 92.4 |
| O | $C_2H_5$ | $C_2H_5$ | H | H | 200 | 0.6 |
| O | $C_2H_5$ | H | 6-$OCH_3$ | H | 200 | 20.9 |
| O | H | H | 5-$OCH_3$ | H | 200 | 82.4 |
| O | $C_2H_5$ | H | 5-$OCH_3$ | H | 200 | 21.7 |
| O | H | $-CH_2C_6H_5$ | H | H | 200 | 48.7* |
| O | H | $CH_3$ | 6-$CH_3$ | 7-$CH_3$ | 200 | 20.9 |
| O | H | $C_2H_5$ | 6-$CH_3$ | 7-$CH_3$ | 200 | 1.4 |
| O | H | H | 5-$CH_3$ | 7-$CH_3$ | 200 | 112.2 |
| O | $CH_3$ | H | 5-$CH_3$ | 7-$CH_3$ | 200 | 95.9 |
| O | H | $OCH_3$ | H | H | 100 | 39.6 |
|   |   |   |   |   | 200 | 61.6 |
|   |   |   |   |   | 400 | 107.9 |
| O | H | H** | H | H | 200 | 197.8 |
| O | H | $CH_3$** | H | H | 200 | 129.5 |
| O | H | $-OCH_2C_6H_5$ | H | H | 400 | 71.7* |

*Average 2 replicates.
**(S) - Optical isomer.

EXAMPLE 26

The following tests are conducted to determine the effect of test compounds on the growth and feed efficiency of feeder lambs when fed at 50 ppm in the diet for eight weeks.

White-faced feeder lambs are housed on outside pads and fed hay and water ad libitum prior to testing. Following an adjustment to concentrate feeding, the sheep are randomly allotted to pens in groups of five and weighed. Three kg of experimental or control diet is placed in each feeder in the morning, and again each evening. The following morning, the feed remaining in each feeder is weighed, saved in a separate bag for each pen, and fresh feed added to each feeder. At weekly intervals, the feed in the waste bags is weighed, and the amount consumed by the sheep in each pen calculated. At the end of the eight-week evaluation, the sheep are weighed, and the gain and feed efficiency for each group determined. Four or five pens of five lambs each per treatment are used. The diet used and the results obtained with representative compounds are reported below.

| Diet (Sheep Ration) Ingredient | % |
|---|---|
| Ground Corn Cob | 35.0 |
| Molasses, Cane | 12.0 |
| Dehydrated Alfalfa Meal (17%) | 20.0 |
| Ground Yellow Corn | 19.0 |
| Soybean Oil Meal (44%) | 12.0 |
| Iodized Salt | 0.5 |
| Dicalcium Phosphate | 1.0 |
| *Premix | 0.5 |
|  | 100.0 |
| *Premix for 1 Ton: |  |
| Trace Minerals + Zinc | 908 grams |
| Vitamin A (30,000 µ/g) | 133 grams |
| Vitamin $D_3$ (200,000 µ/g) | 5 grams |
| Corn Oil | 100 grams |
| Ground Corn | 3394 grams |
| Total | 4540 grams |

TABLE II

| Treatment | Level ppm | Eight-Week Weight Gain (kg/Lamb) Replications | | | | | |
|---|---|---|---|---|---|---|---|
| | | 1 | 2 | 3 | 4 | 5 | Average |
| Control | — | 11.60 | 12.65 | 9.00 | 11.45 | — | 11.175 |
|  | 50 | 12.50 | 11.60 | 9.20 | 13.10 | — | 11.60 |
| Control | — | 14.02 | 11.64 | 11.54 | 11.80 | 13.90 | 12.58 |
|  | 50 | 12.66 | 13.08 | 12.94 | 13.74 | 12.42 | 12.97 |

TABLE III

| Treatment | Level ppm | Eight-Week Feed Efficiency Evaluations (Feed/Gain) Replications | | | | | |
|---|---|---|---|---|---|---|---|
| | | 1 | 2 | 3 | 4 | 5 | Average |
| Control | — | 6.866 | 6.874 | 7.724 | 7.881 | — | 7.336 |
|  | 50 | 7.357 | 7.187 | 7.946 | 6.365 | — | 7.214 |
| Control | — | 7.48 | 8.68 | 7.84 | 7.65 | 7.67 | 7.86 |
|  | 50 | 8.07 | 7.81 | 7.59 | 8.10 | 7.53 | 7.82 |

EXAMPLE 27

The following tests were conducted to determine the effect of test compound administered parenterally as an implant in growth of sheep for eight weeks.

In these tests, two groups of eight lambs are used, with each group containing four females and four castrate males. The lambs are housed individually and fed ad libitum the diet reported below, and water is likewise available ad libitum. Test compound is made into pellets containing 18 mg. of drug and 2 mg. of Carbowax 4000 as a binder, and control animals are implanted with a pellet containing starch and binder. All implants are made at the base of the ear on the first day of the experiment, and lambs receiving test compound are reimplanted every two weeks with approximately 54 mg. of test compound. This provides a total growth factor dose of 226 mg. over a 56-day period, or approximately 4 mg. per lamb per day. With mean lamb weights of about 40 kg, this results in a daily dose of 0.1 mg. per kg. of body weight. Feeding and weighing are done as described in Example 26 above. The testing results with representative compounds are summarized below.

| Diet (Lamb Finishing) | |
|---|---|
| Ingredient | % |
| Ground Corn Cob | 15.0 |
| Ground Yellow Corn | 48.0 |
| Soybean Oil Meal (49%) | 10.0 |

15

-continued

| Diet (Lamb Finishing) Ingredient | % |
|---|---|
| Dehydrated Alfalfa Meal | 15.0 |
| Molasses | 10.0 |
| Iodized Salt | 0.5 |
| Dicalcium Phosphate | 1.0 |
| *Premix | 0.5 |
| | 100.0 |

| *Premix for 1 Ton: | | |
|---|---|---|
| Trace Minerals | 454 | grams |
| Vitamin A (30,000 μ/g) | 133 | grams |
| Vitamin D₃ (200,000 μ/g) | 5 | grams |
| Corn Oil | 100 | grams |
| Ground Corn | 3848 | grams |
| Total | 4540 | grams |

TABLE IV

| | | Eight-Week Weight Gain (kg/Lamb) | | | | | | | | |
|---|---|---|---|---|---|---|---|---|---|---|
| | Level Im-planted | Replications | | | | | | | | |
| Treatment | (mg) | 1 | 2 | 3 | 4 | 5 | 6 | 7 | 8 | Average |
| Control | — | 14.5 | 13.4 | 12.9 | 8.7 | 11.1 | 15.3 | 13.0 | 9.2 | 12.26 |
| 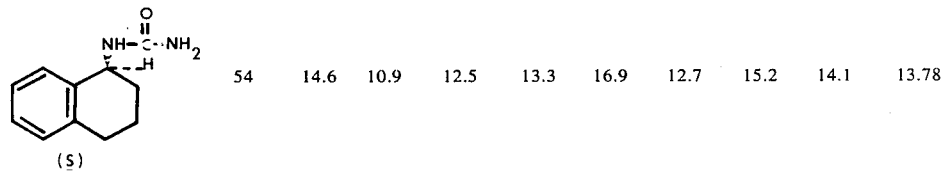 (S) | 54 | 14.6 | 10.9 | 12.5 | 13.3 | 16.9 | 12.7 | 15.2 | 14.1 | 13.78 |

| | | Eight-Week Feed Efficiency Evaluations (Feed/Gain) | | | | | | | | |
|---|---|---|---|---|---|---|---|---|---|---|
| | Level Im-planted | Replications | | | | | | | | |
| Treatment | (mg) | 1 | 2 | 3 | 4 | 5 | 6 | 7 | 8 | Average |
| Control | — | 6.16 | 6.21 | 6.86 | 8.90 | 7.99 | 6.20 | 6.34 | 7.38 | 7.005 |
| 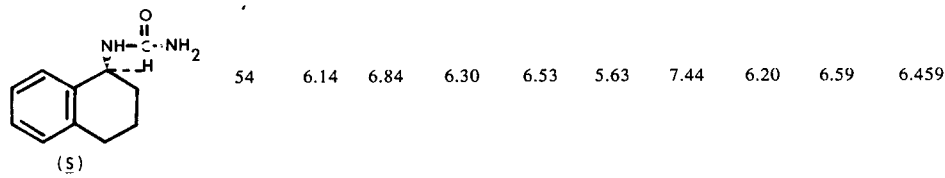 (S) | 54 | 6.14 | 6.84 | 6.30 | 6.53 | 5.63 | 7.44 | 6.20 | 6.59 | 6.459 |

We claim:

1. A method for enhancing the growth rate of ruminant livestock, poultry or fur bearing animals comprising, administering orally or parenterally to said animals a growth-enhancing amount of a racemic mixture or an optically active isomer of a compound of the formula:

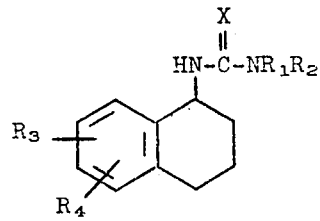

wherein X is a member selected from the group consisting of sulfur and oxygen; $R_1$ is a member selected from the group consisting of hydrogen and alkyl $C_1$–$C_4$; $R_2$ is a member selected from the group consisting of hydrogen, alkyl $C_1$–$C_4$, alkoxy $C_1$–$C_4$, benzyl and benzyloxy; $R_3$ is a member selected from the group consisting of hydrogen, alkyl $C_1$–$C_4$ and alkoxy $C_1$–$C_4$; and $R_4$ is a member selected from the group consisting of hydrogen and alkyl $C_1$–$C_4$.

2. The method of claim 1, wherein $R_3$ and $R_4$ are hydrogen, and X, $R_1$ and $R_2$ are as defined in said claim 1.

3. The method of claim 1, wherein X is oxygen; $R_1$, $R_3$ and $R_4$ are hydrogen; and $R_2$ is alkyl $C_1$–$C_4$.

4. The method of claim 1, wherein X is sulfur; $R_1$, $R_3$ and $R_4$ are hydrogen; and $R_2$ is alkyl $C_1$–$C_4$.

5. The method of claim 1, wherein said compound is in its racemic form.

6. The method of claim 1, wherein X is oxygen; and $R_1$, $R_2$, $R_3$ and $R_4$ are hydrogen.

7. The method of claim 6, wherein said compound is the optically active (S) isomer:

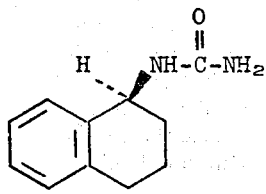

8. The method of claim 1, wherein said compound is administered parenterally to said animal to provide a daily dose level between about 0.001 mg. and 0.2 mg. per kg. of animal body weight.

9. The method of claim 8, wherein said compound is administered as a subcutaneous implant, in solid or paste form.

10. The method of claim 1 wherein said compound is an optically active isomer of the formula:

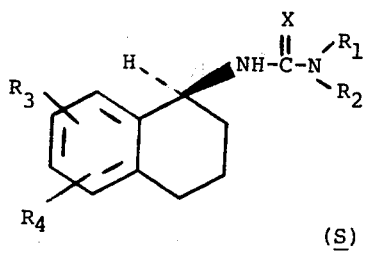

(S)

11. The method of claim 10 wherein said compound is an optically active isomer of the formula:

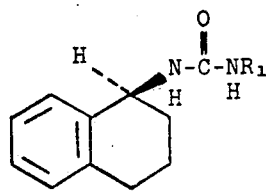

wherein $R_1$ is alkyl $C_1$–$C_4$ and the animal is a ruminant livestock.

12. The method of claim 1, wherein said compound is orally administered to said animals in an amount equivalent to from 25 ppm. to 800 ppm. by weight of the animal feed.

13. An animal feed composition for enhancing the growth rate of ruminant livestock, poultry and fur bearing animals comprising, a nutritionally balanced diet containing from about 25 ppm. to 800 ppm. of a compound of the formula:

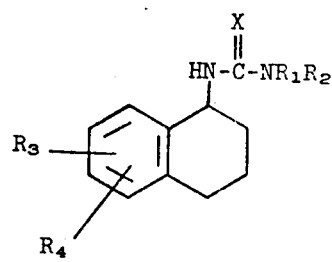

wherein X is sulfur or oxygen; $R_1$ is hydrogen or alkyl $C_1$–$C_4$; $R_2$ is hydrogen, alkyl $C_1$–$C_4$, alkoxy $C_1$–$C_4$, benzyl or benzyloxy; $R_3$ is hydrogen, alkyl $C_1$–$C_4$ or alkoxy $C_1$–$C_4$; and $R_4$ is hydrogen or alkyl $C_1$–$C_4$, or its (S) isomer.

14. The composition of claim 13, containing from 50 ppm. to 200 ppm. of said compound.

* * * * *